(12) United States Patent
Rovati

(10) Patent No.: US 9,062,129 B2
(45) Date of Patent: Jun. 23, 2015

(54) HYALURONIC ACID ESTERS, THEIR PREPARATION AND USE IN DERMATOLOGY

(75) Inventor: Lucio Claudio Rovati, Milan (IT)

(73) Assignee: ROTTAPHARM S.p.A., Milan (IT)

( * ) Notice: Subject to any disclaimer, the term of this patent is extended or adjusted under 35 U.S.C. 154(b) by 71 days.

(21) Appl. No.: 13/468,846

(22) Filed: May 10, 2012

(65) Prior Publication Data

US 2012/0289478 A1  Nov. 15, 2012

(30) Foreign Application Priority Data

May 13, 2011 (IT) ............... TO2011A0428

(51) Int. Cl.

| | | |
|---|---|---|
| *C08B 37/08* | (2006.01) | |
| *A61K 31/728* | (2006.01) | |
| *A61Q 19/00* | (2006.01) | |
| *A61K 8/73* | (2006.01) | |
| *A61K 47/36* | (2006.01) | |
| *C08L 5/08* | (2006.01) | |

(52) U.S. Cl.

CPC .......... *C08B 37/0072* (2013.01); *A61Q 19/007* (2013.01); *A61K 8/735* (2013.01); *A61K 47/36* (2013.01); *A61Q 19/00* (2013.01); *C08L 5/08* (2013.01)

(58) Field of Classification Search

CPC . C08B 31/0072; A61K 31/728; A61Q 19/007
See application file for complete search history.

(56) References Cited

U.S. PATENT DOCUMENTS

| | | | |
|---|---|---|---|
| 4,582,865 A | 4/1986 | Balazs et al. | |
| 5,462,976 A * | 10/1995 | Matsuda et al. | ................ 522/74 |
| 5,679,567 A | 10/1997 | Fleno et al. | |
| 5,977,088 A * | 11/1999 | Harper et al. | ................... 514/54 |
| 6,107,410 A * | 8/2000 | Waki et al. | .................... 525/293 |

FOREIGN PATENT DOCUMENTS

| | | |
|---|---|---|
| EP | 0 341 745 A1 | 11/1989 |
| EP | 0 554 898 A2 | 8/1993 |
| JP | 2004-315386 A | 11/2004 |
| WO | WO 01/67891 A1 | 9/2001 |
| WO | WO 2005/070380 A1 | 8/2005 |
| WO | WO 2005/092929 A1 | 10/2005 |
| WO | WO 2008/081255 A1 | 7/2008 |
| WO | WO 2009/080220 A1 | 7/2009 |

OTHER PUBLICATIONS

Definition of derivative, Free Merriam-Webster Dictionary, www.merriam-webster.com/dictionary/derivative, accessed online on Jan. 29, 2014.*
Lloyd et al., "Carbohydrate polymers as wound management aids", Carb. Polym., 1998, 37, p. 315-322.*
Ishii, T., Plant Science, 1997, 127, p. 111-127.*
Extended European Search Report for corresponding European Patent Application No. 12167497.2 mailed Feb. 19, 2013.
Italian Search Report for corresponding Italian Patent Application No. TO2011A000428 mailed Mar. 19, 2012.
Coradini, D. et al. "Hyaluronic-acid butyric esters as promising antineoplastic agents in human lung carcinoma: A preclinical study", Investigational New Drugs, vol. 22, 2004, pp. 207-217.
Voisin-Chiret, A. et al. "Synthesis of New *L*-Ascorbic Ferulic Acid Hybrids", Molecules, vol. 12, 2007, pp. 2533-2545.
A. Cappelli et al., Hyaluronan Derivatives Bearing Variable Densities of Ferulic Acid Residues, Journal of Materials Chemistry B Accepted Manuscript, Royal Society of Chemistry, published Mar. 27, 2014, 12 pages.

* cited by examiner

*Primary Examiner* — Jonathan S Lau
(74) *Attorney, Agent, or Firm* — Merchant & Gould P.C.

(57) ABSTRACT

New ester derivatives of hyaluronic acid with hydroxy-cinnamic acid, their rheological and anti-radical properties are used as protective agents in dermatology.

14 Claims, 6 Drawing Sheets

HYALURONIC ACID ESTERS, THEIR PREPARATION AND USE IN DERMATOLOGY

This application claims benefit of Serial No. TO2011A000428, filed 13 May 2011 in Italy and which application is incorporated herein by reference. To the extent appropriate, a claim of priority is made to each of the above disclosed applications.

BACKGROUND OF THE INVENTION

The present invention relates to novel ester derivatives of glycosaminoglycanes (GAG) such as hyaluronic acid (HA) with derivatives of hydroxy-cinnamic acid, such as ferulic acid and caffeic acid.

HA is a GAG consisting of a repeating sequence of a disaccharide unit formed by glucuronic acid and N-acetyl-glucosamine.

HA carries out several biological functions, which span from the regulation of the water present in the tissues to the cellular motility and also has, in the derma, a function as a supporting scaffold by binding with other substances to form macromolecular complexes which provide compactness to the skin.

The hydroxy-cinnamic acid derivatives such as ferulic acid and caffeic acid are widely distributed within the seeds and the leaves of the vegetable world in a free form or covalently bonded with lignine or other biopolymers. Owing to the phenolic nucleous and to the extended conjugation of the side chain, they form phenoxy radicals, which are stabilised by resonance which generate their potent antioxidant and protective function in various inflammatory pathologies and in the protective property of cells exposed to ultraviolet radiations.

Hyaluronic acid is a moisturizing substance which, at the skin level, acts by retaining transepidermic water. It is however a highly hydrophilic molecule which penetrates with difficulty into the highly lipidic horny layer and it is moreover a substance which is subject to rapid degradation. One of the advantages of the compounds of the present invention is that the presence of hydroxy-cinnamic substituents of the modified polymer provides protection from enzymatic degradation operated by hyaluronidase which is present in the tissues; moreover, the esterification of HA with the hydroxy-cinnamic acid derivatives has allowed to obtain compounds with enhanced lipophilic properties, with respect to the native polimer and which can therefore be more easily bio-absorbed through the epidermis.

In view of its chemical, physical and biological properties, HA has been particularly studied and has been the subject of structural modifications and there are several publications and patents relating to new derivatives.

Several works were carried out on processes for reticulation of HA so as to obtain viscoelastic products to be used primarily for intra-articular administration in the arthrosis therapy, such as described, for instance, by EP 0 341 745, or to be used also as a post-surgical anti-adhesive, as described e.g. by U.S. Pat. No. 4,582,865.

Relatively lower is the number of patents or publications relating to esters obtained on the hydroxy groups of HA with organic acids.

Among these we can refer to U.S. Pat. No. 5,679,567, which describes the preparation of acetylated HA with different substitution degrees. WO2005/092929 and Inv. New Drugs (2004), 22 (3), 207-217, describe ester derivatives of HA with butyrric acid, which are endowed with anti-proliferative activity and which are therefore potentially useful for antitumoral use, whereas WO2008/081255 describes other ester derivatives of HA with butyrric acid, but with a high reticulation degree and which are to be used primarily as viscosity-elasticity enhancing agents for intra-articular administration. Other ester derivatives of HA are described by Picotti et al. in WO2009/080220, wherein HA is esterified with the lipoic acid to provide derivatives for dermocosmetic use or as a medical device for intra-articular treatment.

In our knowledge, up to now, there is no description of polysaccharide esters and more specifically of esters of HA with hydroxy-cinnamic acid derivatives, such as ferulic and caffeic acid for dermoprotective use as compounds having elasticity-enhancing, moisturising, softening activity or for use as medical devices with anti-reddening or soothing activity of the herythematous conditions induced by radiation or as viscosity-supplementing agents.

SUMMARY OF THE INVENTION

The present in invention describes novel ester derivatives of hyaluronic acid with derivatives of hydroxy-cinnamic acid, such as ferulic and caffeic acid, different from the previously cited polysaccharide derivatives which were esterified with different acids such as acetic, butyrric and lipoic acid.

The substitution degree of the esterified hyaluronic acid according to the invention can be adjusted and depends on the applied reaction conditions such as, by way of example, on the stechiometric ratio between hyaluronic acid and the hydroxy-cinnamic acid derivative pre-activated with carbonyl-di-imidazole, the amount of the catalytic base which is used and the time of reaction and is comprised, within the scope of the investigated experimental conditions, between 2% and 20%.

The chemical, physical and rheological features of the derivatives obtained according to the invention can be changed, therefore, by changing the esterification degree of the hyaluronic acid with the hydroxy-cinnamic acid component. Such derivatives can be topically used as moisturising, elasticity-enhancing, anti-aging, anti-acne agents or also for the treatment of skin injuries of different nature such as wounds, atopic dermatitis, skin hyperthermias induced by radiations of different nature.

The invention also relates to a method for preparing such derivatives, which is different and novel with respect to the prior art. Such a method in fact contemplates a recovery of the reaction products by means of precipitation with acetone, followed by purification by treatment with methanol, filtration and drying under vacuum, which allows to remove the impurities of the synthesis process without the need to use time-consuming and expensive processes such as dialysis or tangential filtration, with the subsequent recovery of the final desired product by means of lyophilisation or spray drying.

DETAILED DESCRIPTION

EXAMPLES

The NMR experiments were recorded by using a Bruker Advance 400 instrument. The compounds were dissolved in $D_2O$ at pH 12 with the use of a drop of KOD with a concentration of about 5 mg/ml.

In the aromatic zone comprised between 6 and 8 ppm one can observe the aromatic signals due to the esterification, whereas the very strong signal of the methyl singlet of hyaluronic acid is visible at about 1.8 ppm. The integration of these signals provides the esterification degree of the samples.

Example 1

Preparation of the Ferulic Acid Ester of Hyaluronic Acid with a Medium Degree of Substitution (Compound 1)

3 g of Na hyaluronate (mw 404; 7.9 meq. in monomeric units, molecular weight of 300 kD) are dissolved at 90° C. in 60 ml of formamide. After cooling at room temperature 1.05 ml triethylamine (7.5 meq.) and 0.5 g feruloylimidazolide (mw 244; 1.99 meq.) suspended in 10 ml formamide and prepared as described in Molecules 2007, 12, p. 2540-2544, compound 12, are added to the thus obtained solution.

After overnight reaction at room temperature, the reaction mixture is diluted with 15 ml of 5% NaCl. The initially highly viscous solution, which has thus become more fluid, is poured drop-wise in 1 liter of anhydrous acetone. The thus obtained precipitate is filtered, subjected again to stirring with 400 ml anhydrous acetone, re-filtered and again stirred with 200 ml of anhydrous methanol.

After filtering and drying under vacuum at 40° C., 3.1 g of anhydrous sample are recovered.

The thus obtained compound is analysed by means of IR, NMR spectroscopy and elemental analysis.

Figure 1:
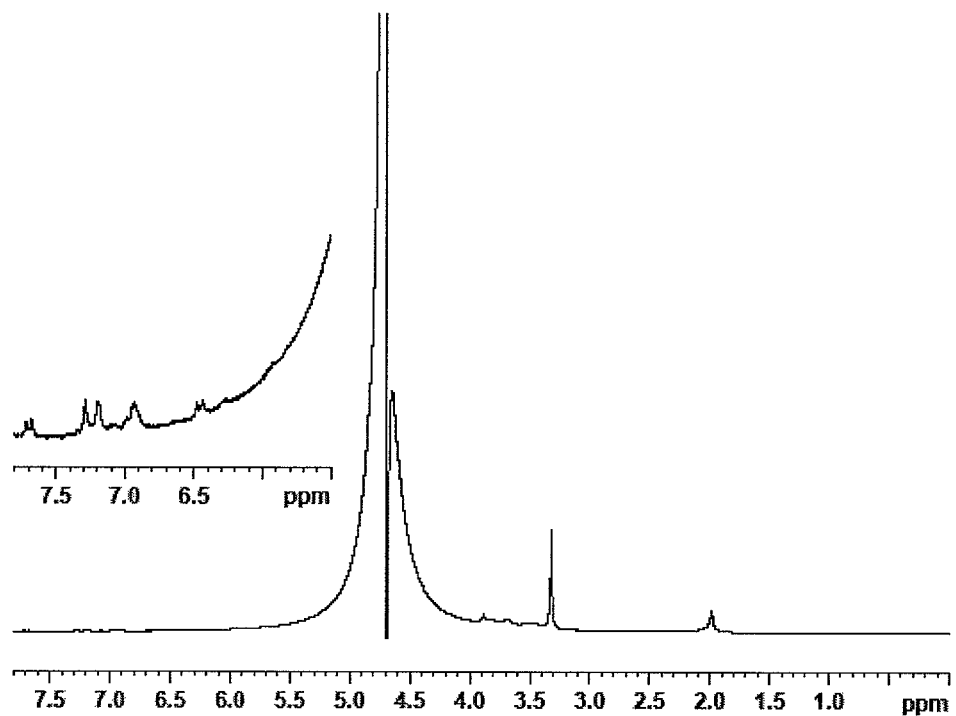
FIG. 1 is a plot of nuclear magnetic resonance signals versus concentration for example 1.

A substitution degree (esterification) of 8% was obtained, by calculating the ratio of the integration signals (NMR) between the signal of the methyl group of HA and the doublet signal of ferulic acid (cf. NMR of FIG. 1).

Example 2

Figure 2:
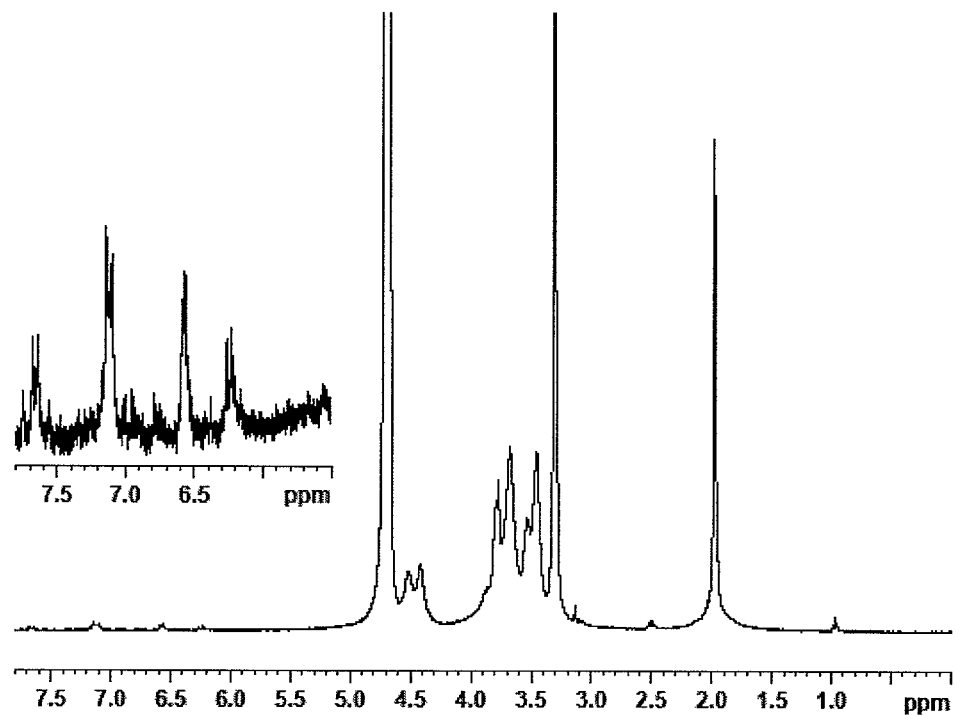
FIG. 2 is a plot of nuclear magnetic resonance signals versus concentration for example 2.

Preparation of the Ferulic Acid Ester of Hyaluronic Acid with a Low Substitution Degree The same procedure of example 1 is followed, however reducing the reaction time before the addition of NaCl to only 2 hours. 2.8 g of the anhydrous compound are obtained with an esterification degree of 4% (cf. NMR FIG. 2).

Example 3

Figure 3:
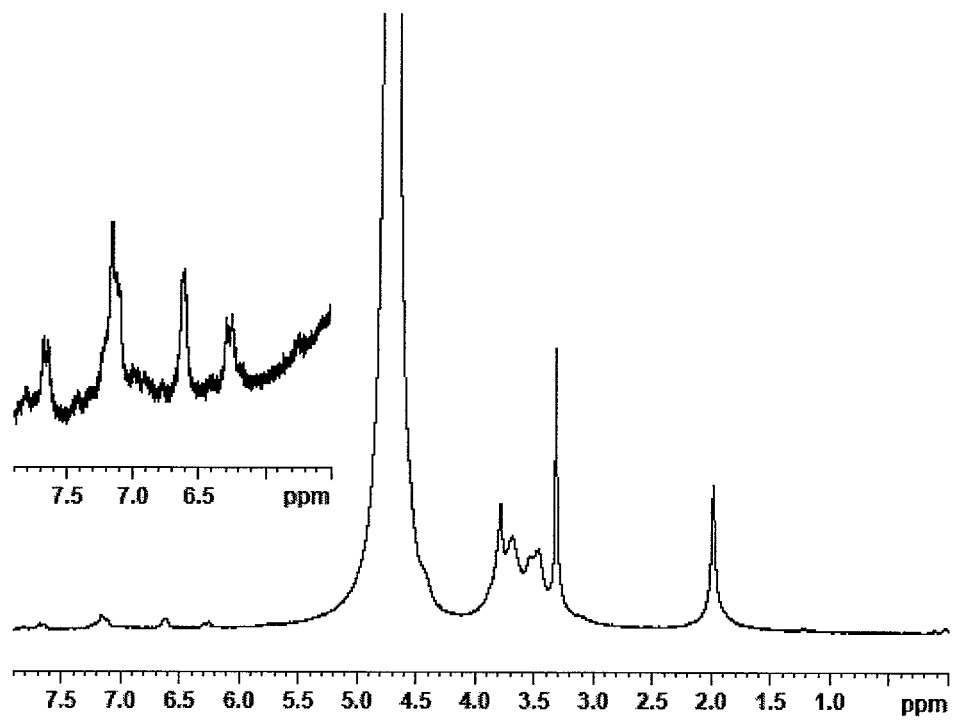
FIG. 3 is a plot of nuclear magnetic resonance signals versus concentration for example 3.

Preparation of the Ferulic Acid Ester of Hyaluronic Acid with a High Substitution Degree The procedure of example 1 is followed, however increasing the reaction time before the addition of NaCl to 24 hours and the amount of imidazolide to 1.9 g (7.9 meq.). 3.3 g of the anhydrous compound are obtained with an esterification degree of 17% (cf. NMR FIG. 3).

Example 4

Preparation of the Caffeic Acid Ester of Hyaluronic Acid

To a solution of caffeic acid (0.51 g, 2.83 mmoles) in anhydrous THF (10 ml), 1,1'-carbonyldiimidazole (CDI, 0.92 g, 5.67 mmoles) are added. The resulting mixture was maintained under reflux for 1 h and the reaction mixture was directly used in the following step.

Sodium hyaluronate (3.0 g, 7.92 mmoles in monomeric units) was dissolved in formamide (60 ml) at 70° C. in 1 h in a 2-neck balloon placed in a sand bath. The thus obtained viscous and colourless solution was cooled at room temperature and added with TEA (1.1 ml, 7.92 mmoles) and with the solution in THF of imidazolide (about 2.8 mmoles). The mixture was stirred until a homogenous orange-reddish solution was obtained. The viscosity and the consistency of the solution increased to such a point to lead in few minutes to the formation of a gelatinous orange-reddish (rubbish rubbery and elastic) agglomerate. After having been maintained under rest at room temperature overnight, the agglomerate was added to a solution of NaCl 5% w/v (15 ml).

The obtained gel was treated with 200 ml acetone, filtered, re-suspended under stirring twice with 100 ml methanol, filtered and dried under vacuum. 2.5 g of anhydrous product with yellow ochre colour were obtained.

Figure 4:
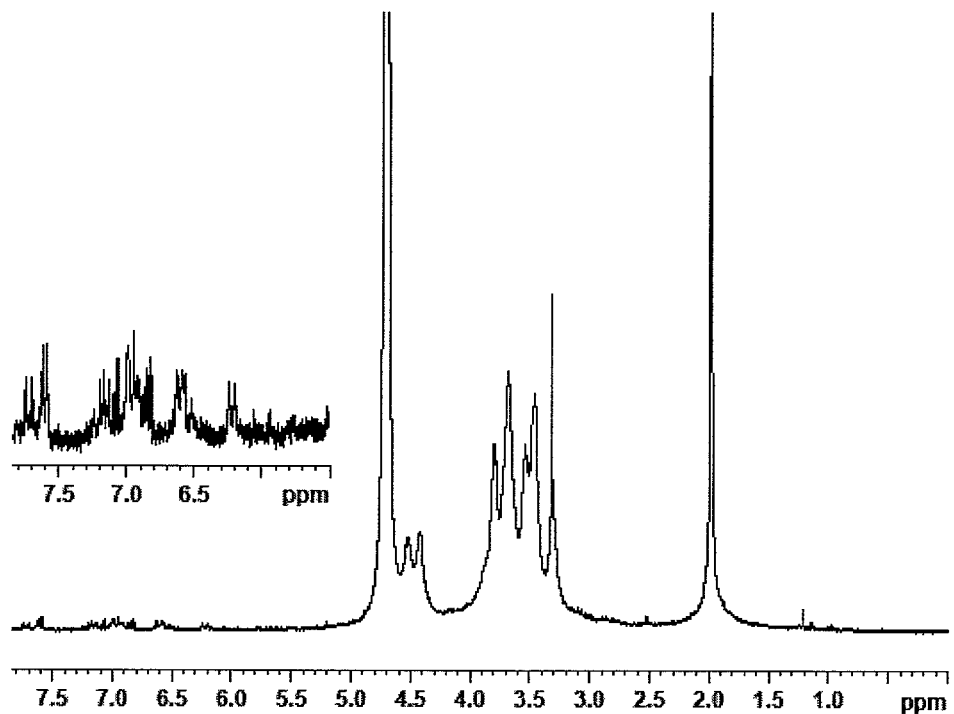
FIG. 4 is a plot of nuclear magnetic resonance signals versus concentration for example 1.

A sample of about 6 mg of the polymer was let to swell in a 0.7 ml $D_2O$ to obtain a perfectly transparent and colourless gel. The gel was transferred into a NMR tube and the analysis (FIG. 4) showed the doublet signals between 6 and 7.2 ppm, which can be attributed to the aromatic hydrogens of the esterified caffeic acid and the strong singlet signal of the methyl group at 1.8 ppm. The addition of one drop of NaOD at 40% in $D_2O$ allowed to quantify the derivatisation degree of sodium hyaluronate, which was found to be equal to 7%.

Example 5

Evaluation of the Resistance Against Enzymatic Degradation

The presence of microorganisms on the epidermis causes a relevant biological activity on the skin, an activity which is shown in the form of various enzymatic functions, among which that carried out by the hyaluronidase enzyme. Hyaluronic acid (HA) is naturally degraded due to the presence of said enzyme, which catalyses its degradation by means of the hydrolysis of the glycosidic 1.4 beta bonds between the monomeric units of the polysaccharide chain. Cross-linked HA is highly resistant to the enzymatic action of hyaluronidase and such a resistance increases with increasing the cross-linking degree. The esterification of HA with molecules having a suitable chemical structure such as the derivatives of hydroxy-cinnamic acid according to the invention has allowed to obtain compounds with rheological features which can be compared to cross-linked HA, however maintaining a goods solubility degree in water.

Commercial sodium salt of HA (molecular weight 300 kD), such as used in the previously described synthesis, and two samples of HA esterified with ferulic acid with a low and high esterification degree as described respectively in examples 2 and 3 above, were used.

The experiment was carried out according to conventional procedures.

Shortly, a polysaccharide solution (1 mg/ml) maintained at 37° C. and containing the enzyme in an amount equal to 0.1 mg/ml (bovine testicular hyaluronidase, type I-S, Sigma, 1000 U/mg) was incubated at 37° C. At regular time intervals, in the range 0-2 hours, samples in the amount of 0.5 ml were taken and were put at 100° C. for 5 minutes, filtered to remove the enzyme and thereafter analysed by means of size exclusion chromatographic analysis: processing of the chromatogram allows to determine the molecular weight distribution.

After 30 minutes of incubation with the enzyme, commercial non-esterified HA underwent a strong degradation, changing from an average molecular weight of about 300 kD to a value about 10 times lower. The sample relating to example 2, with an esterification degree of about 4%, underwent a degradation of about 60%, whereas the sample relating to example 3, with a high esterification degree, underwent only a limited degradation process changing to an average molecular weight of about 250 kD.

Example 6

Rheological Study on a Sample of HA Esterified with Ferulic Acid

The rheological behaviour of a compound according to the invention (compound of example 1) was compared with that of the sodium salt of HA (molecular weight 300 kD) used as the raw starting material for the preparation of the esters according to the invention.

The rheological measurements were carried out using the Rotovisco 1-Haake rheometer, plate/plate system, Rheowin 323 software. The viscosity was measured by means of velocity gradient of the disc, "shear rate", from 0.01 $s^{-1}$ to 500 $s^{-1}$ and the samples were dissolved in the amount of 2% in NaCl 5% saline solution.

Figure 5A:
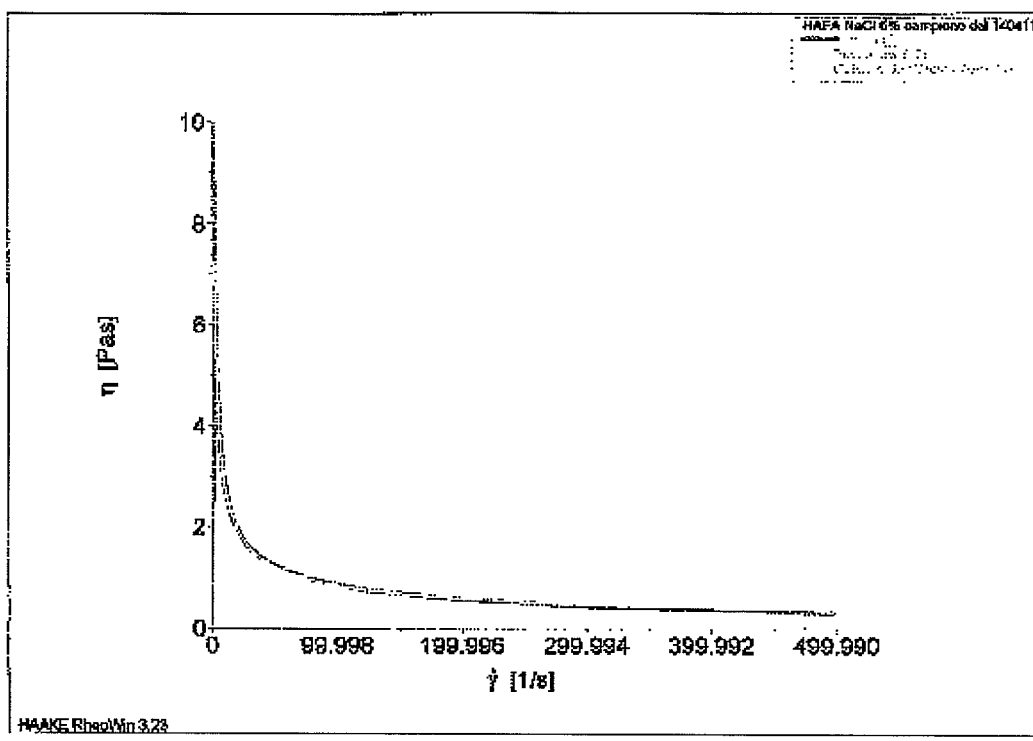
FIGS. 5a and 5b are plots showing viscosity versus shear rate for example 1.
Figure 5B:
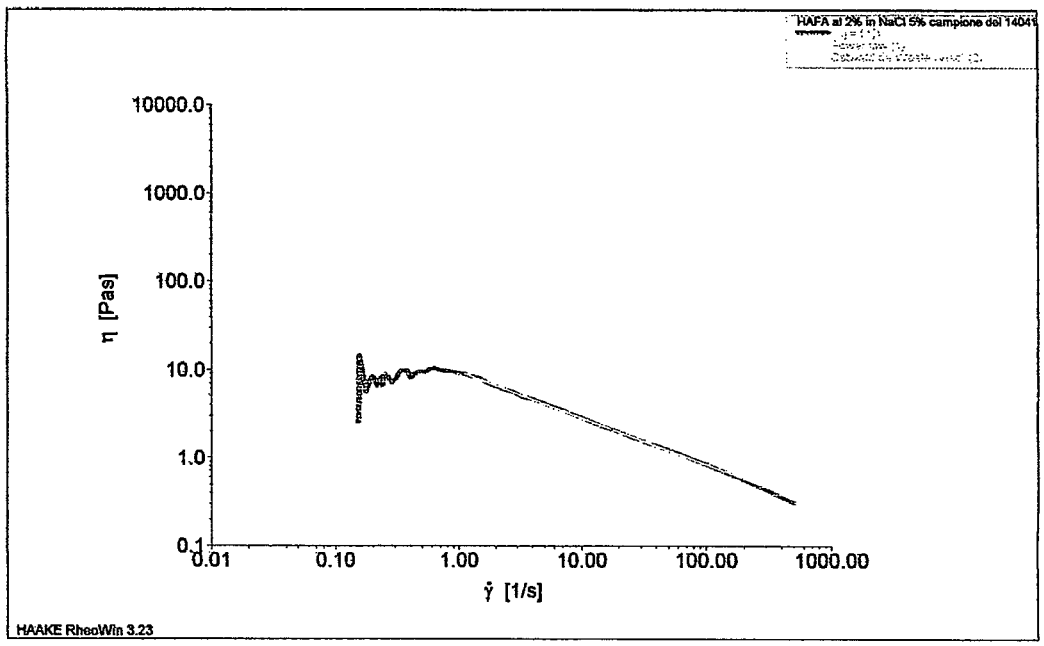

The sample relating to example 1 showed a rheological behaviour of the pseudo-plastic type, wherein the viscosity decreases with increasing shear rate (cf. FIGS. 5a and 5b). The calculated parameters of the flow diagram, obtained by applying the Ostwald de Waele relationship, were respectively: K (Pa·s), that is, flow consistency index equal to 9.97+/−0.53 (n=3) and n=0.47 (flow behaviour index, that is the slope of the viscosity curve, in a logarithmic scale, as a function of the velocity gradient).

In practice, this result leads to conclude that the esterification of HA with ferulic acid provides chains which at low shears have non-negligible non-linear hindrance conformations, which can interact with each other. By increasing the applied shear, the chains tend to align with the flow, thus reverting the system to the native behaviour.

To the contrary, non-modified native HA has a profile typical of the solutions, with a very low K value (K=0.40 Pa·s).

Example 7

Anti-ROS activity of the Compound HA ferulate (Example 1) on Activated Human Neutrophils It was investigated if the compounds according to the invention could maintain the anti-oxidant anti-radical scavenging activity of the hydroxy-cinnamic acids substrates used for the esterification of HA.

We have studied the capacity of compound 1 of inhibiting, in vitro, the activity of oxygen reactive molecules (ROS) produced by human neutrophil leucocytes, activated by Phorbol-Miristate-Acetate (PMA) in the presence of Luminol, a substance which in the presence of oxydants, such as $H_2O_2$, exhibits chemiluminescence.

Accordingly, amounts of cell suspensions of leucocytes ($10^6$ cell/ml) were incubated with compound 1 dissolved in a suitable buffer in the presence of Luminol (5 µM). The cells were incubated at 37° C. for 10 minutes with compound 1 or with native sodium salt of HA at the concentration of 0.02 and 0.2 mM. Thereafter, the cells were activated with 0.1 PMA and the chemiluminescence was monitored for 20 minutes at time intervals of 4 minutes with the fluorescence reader HTS7000 (Perkin Elmer).

Compound 1 showed a maximum of inhibition of 78% at the higher tested concentration, whereas HA was practically inactive, showing that the introduction of ferulic acid in the polysaccharide lowered the anti-radical activity of the starting substrate.

Example 8

Preparation of an O/W Softening Cream with a Solar Filter

As a non-limiting example of the invention, a cream formulation was prepared containing an ester derivative according to the invention, strengthened by the addition of a substance endowed with a solar protection factor (UVB) such as gamma-oryzanol, thereby to integrate the action of the cromophore moiety in the modified polysaccharide.

The formulation contains compound 1 described in example 1 at a concentration of 2%, mixed with conventional excipients used in dermatology, such as emulsifying agents, preservatives, soothing agents, solvents and a product having a protective activity against solar radiations, namely gamma-oryzanol.

Briefly, the preparation process was the following:

a) fat phase: di-caprilyl carbonate, coco-caprylate, polyglyceryl-2-dipolyhydroxystearate and phenoxy-ethanol were dissolved under stirring by heating to about 80° C. in a dissolver; following dissolution, gamma-oryzanol was added;

b) aqueous phase: water, sodium dehydroacetate and compound 1 were charged into a turbo emulsifier; after heating to about 60° C. until dissolution, additional components were added always under light stirring, namely the emulsifying mixture sodium lauryl glucose carbossilate/lauryl glucoside and the preservative mixture methylpropanediol/phenylpropanol;

c) emulsion: the fat phase was poured under stirring into the aqueous phase and the turbine was activated for 10 minutes; the reaction mass was eventually slowly cooled always under stirring, down to the temperature of 20/25° C.

A cream having the following composition (% by weight) was obtained:

| Compound 1 | | 2 |
|---|---|---|
| Dicaprylyl carbonate | Soothing agent | 10 |
| Coco-caprylate | Soothing agent | 10 |
| Polyglic.-dipolyhydroxystearate | Emulsifying agent | 8 |
| Phenoxy-ethanol | Preservative | 1 |
| Gamma-oryzanol | UVB Filter | 4 |
| Sodium-dehydroacetate | Preservative | 0.5 |
| Methylpropanediol/phenylpropanol | Preservative | 1.5 |
| Sodiumlaurylglucose carboxilate | Emulsifying agent | 1.5 |
| Laurylglucoside | Emulsifying agent | 1.5 |
| Water quod sufficit to 100. | | |

Example 9

Functional Assay of the Dermocosmetic Activity

The dermocosmetic functional activities such as skin hydration and elasticity were investigated with the use of the prototype formulation shown in the preceding examples, with a panel of purposely trained volunteers. In the study the activity of the formulation of example 8 was compared with the same formulation without the active ingredient (Control) on two groups of volunteers treated twice a day for a period of 4 weeks (times T0 and T4w).

a) Skin elasticity: the evaluation of the skin elasticity was carried out with the "skin meter", a measurement instrument which, by means of a probe applied to the skin, produces within the probe itself a negative pressure (suction) for a duration of 1 second, followed by release. The elasticity is calculated by the ratio between the residual deformation and the maximum extension of the skin. Such a ratio, known in literature as parameter R2, shows the capacity of the skin to return to its original rest status following a stressing event. The more is such a value close to 1, the higher is the elasticity of the skin.

The treatment of the group relating to the formulation of example 8 gave a percent variation of the R2 parameter at time T4w referred to the initial time T0 of 27.5% ($p<0.05$ t test), whereas the same percent variation for the Control group was found not to be significant. Such a result has shown the compound 1 according to the invention is endowed with a relevant elasticity enhancing activity resulting in the increase of the R2 parameter which was not found in the Control group prepared with the same excipients.

b) Skin hydration: the hydration level of the face skin was measured with a "corneometer", an instrument which measures the skin hydration based on the physical principle of capacitance. The instrument consists of a square sensor with an area of 49 mm$^2$. By pressing the sensor surface on a flat area of the skin of the face, the instrument provides a number proportional to the water content of the horny layer. The number provides therefore the measure of the skin hydration of the skin surface expressed as corneometric units (from 0 to 150 c.u.), which are arbitrary units of the instrument.

At the end of the test, the group treated with the formulation of example 8 recorded an increase of the percent variation of the skin hydration values equal to 4.8% against no variation of the Control group used for comparison. Such an increase was found, however, to be close to the significance limit, a result which is probably due to the relatively low number of the members of the used panel (n=10).

What is claimed is:

1. Hyaluronic acid esters of hydroxy derivatives of cinnamic acid, wherein the hydroxy derivatives of cinnamic acid are selected from the group consisting of ferulic acid and caffeic acid, wherein the molecular weight of hyaluronic acid is between 200,000 and 400,000 Daltons, and wherein the degree of substitution of caffeic or ferulic acids on the hyaluronic acid is between 2% and 20%.

2. Esters of hyaluronic acid according to claim 1, wherein the compound is salified with sodium.

3. A composition comprising hyaluronic acid esters according to claim 1, wherein the composition is formulated for use as an intra-articular viscosity supplementing agent.

4. A topical composition comprising hyaluronic acid esters according to claim 1, wherein the topical composition is formulated for treatment of skin lesions selected from a group consisting of wounds, ulcers, dermatitis, psoriasis, and hyperthermia induced by radiation.

5. Topical compositions comprising hyaluronic acid esters according to claim 1, and dermatologically acceptable inert excipients.

6. Topical compositions according to claim 5, including a percentage of hyaluronic acid ester between 0.1% and 5% by weight of the composition.

7. Topical compositions according to claim 5 in the form of cream, gel, ointment, aqueous or hydro-alcoholic lotion, oil/water or water/oil emulsion.

8. A topical composition comprising esters of hyaluronic acid and ferulic acid or caffeic acid, wherein the molecular weight of hyaluronic acid is between 200,000 and 400,000 Daltons, wherein the degree of substitution of caffeic or ferulic acids on the hyaluronic acid is between 2% and 8%, wherein the composition is formulated for use as a moisturizer, elasticity agent, anti-aging agent or anti-acne agent.

9. The topical composition of claim 8, wherein the composition comprises about 0.1-5 wt-% of the esters, and wherein the composition is capable of improving elasticity of skin.

10. A process for the preparation of esters of hyaluronic acid (HA) according to claim 1, wherein a hyaluronic acid sodium salt is dissolved in formamide, said salt is reacted in the presence of a tertiary base with a derivative of hydroxy-cinnamic acid previously activated with carbonyl-di-imidazole (CDI) at room temperature, the reaction mixture is diluted with an aqueous solution of NaCl, the reaction product is recovered by precipitation with acetone, followed by purification with methanol, filtration and drying under vacuum.

11. Process according to claim 10, in which the derivative of hydroxy-cinnamic acid is ferulic acid.

12. Process according to claim 10, in which the derivative of hydroxy-cinnamic acid is caffeic acid.

13. Process according to claim 10, in which the acid activated with CDI is present in a ratio with respect to HA between 0.25 and 1 equivalent depending upon the desired degree of esterification which is comprised between 2% and 20%.

14. Process according to claim 10, in which HA is allowed to react with the acid activated with CDI for a time between 1 and 24 hours depending on the degree of esterification that is desired, between 2% and 20%.

* * * * *